(12) United States Patent
Kuduvalli et al.

(10) Patent No.: US 8,280,491 B2
(45) Date of Patent: *Oct. 2, 2012

(54) IMAGE GUIDED RADIOSURGERY METHOD AND APPARATUS USING REGISTRATION OF 2D RADIOGRAPHIC IMAGES WITH DIGITALLY RECONSTRUCTED RADIOGRAPHS OF 3D SCAN DATA

(75) Inventors: Gopinath Kuduvalli, San Jose, CA (US); Dongshan Fu, Santa Clara, CA (US); Shehrzad Qureshi, Palo Alto, CA (US)

(73) Assignee: Accuray Incorporated, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/793,621

(22) Filed: Jun. 3, 2010

(65) Prior Publication Data
US 2010/0239153 A1 Sep. 23, 2010

Related U.S. Application Data

(63) Continuation of application No. 10/652,785, filed on Aug. 29, 2003, now Pat. No. 7,756,567.

(51) Int. Cl.
*A61B 5/05* (2006.01)
(52) U.S. Cl. ........ 600/427; 600/429; 600/424; 600/407; 606/33; 606/130
(58) Field of Classification Search .............. 600/427, 600/407, 417, 429; 606/33
See application file for complete search history.

(56) References Cited

U.S. PATENT DOCUMENTS

| | | |
|---|---|---|
| 5,117,829 A | 6/1992 | Miller et al. |
| 5,901,199 A | 5/1999 | Murphy et al. |
| 5,954,647 A | 9/1999 | Bova et al. |
| 6,125,164 A | 9/2000 | Murphy et al. |
| 6,235,038 B1 | 5/2001 | Hunter et al. |
| 6,307,914 B1 | 10/2001 | Kunieda et al. |
| 6,470,207 B1 | 10/2002 | Simon et al. |
| 6,501,981 B1 | 12/2002 | Schweikard et al. |
| 6,516,046 B1 | 2/2003 | Frohlich et al. |

(Continued)

OTHER PUBLICATIONS

International Search Report, International Application No. PCT/US04/27158, International filing date Aug. 20, 2004, mailed Sep. 6, 2005, 16 pages.

(Continued)

*Primary Examiner* — Brian Casler
*Assistant Examiner* — Joel Lamprecht
(74) *Attorney, Agent, or Firm* — Lowenstein Sandler PC (57) ABSTRACT

A set of 2D reconstructed images is generated from a pretreatment 3D scan showing an initial position of a target, wherein the set of 2D reconstructed images corresponds to perturbations from said initial position along fewer than six degrees of freedom. Said set of 2D reconstructed images are registered with one or more 2D x-ray images of said target showing a current position of the target, wherein the registering includes computing a set of 3D transformation parameters that represent a change in position of said target between said initial position of said pretreatment 3D scan and said current position of said 2D x-ray images along six degrees of freedom. A positioning system is instructed to adjust a relative position of a radiosurgical beam generator to said target by an amount prescribed by said 3D transformation parameters, wherein said target is allowed six degrees of freedom of position.

20 Claims, 3 Drawing Sheets

U.S. PATENT DOCUMENTS

| | | | |
|---|---|---|---|
| 6,597,818 | B2 | 7/2003 | Kumar et al. |
| 6,665,555 | B2 | 12/2003 | Henderson et al. |
| 6,782,287 | B2 | 8/2004 | Grzeszczuk et al. |
| 6,907,281 | B2 | 6/2005 | Grzeszczuk et al. |
| 7,024,237 | B1 | 4/2006 | Bova et al. |
| 7,171,257 | B2 | 1/2007 | Thomson |
| 7,187,792 | B2 | 3/2007 | Fu et al. |
| 7,204,640 | B2 | 4/2007 | Fu et al. |
| 7,327,865 | B2 | 2/2008 | Fu et al. |
| 7,480,399 | B2 | 1/2009 | Fu et al. |
| 7,522,779 | B2 | 4/2009 | Fu et al. |
| 2002/0077543 | A1 | 6/2002 | Grzeszczuk et al. |
| 2004/0092815 | A1 | 5/2004 | Schweikard et al. |
| 2004/0131150 | A1 | 7/2004 | Pankratov et al. |
| 2004/0267113 | A1 | 12/2004 | Thomson |
| 2005/0047544 | A1 | 3/2005 | Fu et al. |
| 2005/0049477 | A1 | 3/2005 | Fu et al. |
| 2005/0049478 | A1 | 3/2005 | Kuduvalli et al. |

OTHER PUBLICATIONS

L. Zöllei et al., "2D-3D Rigid Registration of X-Ray Fluoroscopy and CT Images Using Mutual Information and Sparsely Sampled Histogram Estimators", Proceedings 2001 IEEE Conference on Computer Vision and Pattern Recognition, vol. 2, Dec. 8, 2001, pp. 696-703, ISBN: 978-0-7695-1272-3.

L. Zöllei et al., "2D-3D Rigid-Body Registration of X-Ray Fluoroscopy and CT Images", Thesis at the Massachusetts Institute of Technology, Aug. 1, 2001, pp. 1-113.

Bifulco, Paolo, et al, Estimation of out-of-plane vertebra rotations on radiographic projections using CT data: a simulation study, Medical Engineering and Physics 24 (2002), pp. 295-300.

Coste-Maniere, E., "Robotic whole body stereotactic radiosurgery: clinical advantages of the CyberKnife® integrated system", The International Journal of Medical Robotics +Computer Assisted Surgery, 2005, www.roboticpublications.com, pp. 28-39.

Gustafsson, Adaptive Filtering and Change Detection, 2001, Wiley, ISBN: 9780471492870 Online ISBN: 9780470841617, pp. 126.

Maintz, J.B.A., et al., A survey of medical image registration, Medical Image Analysis, vol. 2, 1998, pp. 1-37.

Martin J. Murphy, "An automatic six-degree-of-freedom image registration algorithm for image-guided frameless stereotaxic radiosurgery," Med. Phys. 24(6), 857-866, Jun. 1997.

McLaughlin, R., et al., "A comparison of intensity-based registration and feature-based registration for neurointervention," in Lecture Notes in Computer Science, T. Dohi and R. Kikinis, Eds. Berlin, Germany: Springer—Verlag, 2002, vol. 2489, Proc. MICCAI'02, pp. 517524.

Penney, Graeme P., et al., "Validation of a two- to three-dimensional registration algorithm for aligning preoperative CT images and intraoperative fluoroscopy images," Med. Phys. 28(6), 1024-1032, Jun. 2001.

Penny, Graeme P., et al., °A Comparison of Similarity Measures for Use in 2-D-3-D Medical Image Registration, IEEE Transactions on Medical Imaging, vol. 17, No. 4, Aug. 1998.

Sarrut, D., et al., "Patient positioning in radiotherapy by registration of 2D portal to 3D CT images by a contend-based research with similarity measures," CARS 2000, 707-712.

Weese, J., et al., "Fast Voxel-Based 2D/3D Registration Using a Volume Rendering Method Based on Sharp-Warp Factorization" in SPIE Medical Imaging 1999: Image Processing, 1999, pp. 802-810.

Wein, Wolfgang, "Intensity Based Rigid 2D-3D Registration Algorithms for Radiation Therapy", Dec. 15, 2003, 100 pages.

IMAGE GUIDED RADIOSURGERY METHOD AND APPARATUS USING REGISTRATION OF 2D RADIOGRAPHIC IMAGES WITH DIGITALLY RECONSTRUCTED RADIOGRAPHS OF 3D SCAN DATA

RELATED PATENT APPLICATIONS

The present patent application is a continuation application of U.S. patent application Ser. No. 10/652,785, filed Aug. 29, 2003, entitled, "IMAGE GUIDED RADIOSURGERY METHOD AND APPARATUS USING REGISTRATION OF 2D RADIOGRAPHIC IMAGES WITH DIGITALLY RECONSTRUCTED RADIOGRAPHS OF 3D SCAN DATA," which is incorporated by reference.

FIELD OF THE INVENTION

The present invention relates to radiosurgery. In particular, the present invention relates to an image guided radiosurgery method and apparatus using 2D/3D image registration.

BACKGROUND

Radiosurgery is used to treat tumors and other lesions by delivering a prescribed high dose of high-energy radiation to the target area while minimizing radiation exposure to the surrounding tissue. In radiosurgery, precisely focused beams of radiation (e.g. very intense x-ray beams) are delivered to a target region in order to destroy tumors or to perform other types of treatment. The goal is to apply a lethal amount of radiation to one or more tumors, without damaging the surrounding healthy tissue. Radiosurgery therefore calls for an ability to accurately target a tumor, so as to deliver high doses of radiation in such a way as to cause only the tumor to receive the desired dose, while avoiding critical structures such as the spinal cord.

Conventional radiosurgery uses a rigid and invasive stereotactic frame to immobilize the patient prior to diagnostic CT or MRI scanning. The treatment planning is then conducted from the diagnostic images. The treatment planning software determines the number, intensity, and direction of the radiosurgical beams that should be cross-fired at the target, in order to ensure that a sufficient dose is administered throughout the tumor so as to destroy it, without damaging adjacent healthy tissue. Radiation treatment is typically accomplished on the same day treatment planning takes place. Immobilization of patient is necessary in order to maintain the spatial relationship between the target and the radiation source to ensure accurate dose delivery. The frame is fixed on the patient during the whole treatment process.

Image-guided radiosurgery eliminates the use of invasive frame fixation during treatment, by frequently and quasi-continuously correcting patient position or aligning radiation beam with the patient target. To correct patient position or align radiation beam, the patient pose during treatment needs to be detected. This is accomplished by registering the X-ray image acquired at the treatment time with the diagnostic 3D scan data (e.g., CT, MRI, or PET scan data) obtained pre-operatively at the time of treatment planning. The positions of the target are defined by physicians at the time of treatment planning, using the diagnostic 3D scan. The 3D scan data are used as a reference, in order to determine the patient position change during treatment. Typically, digitally reconstructed radiographs (DRRs) are generated from the 3D scan data, and are used as 2D reference images. Similarity measures are used to compare the image intensities in the x-ray images and the DRR images, in order to determine the change in the position of the patient and the treatment target. In the field of medical image registration, this problem is categorized as a 2D/3D registration.

Image-guided radiosurgery requires precise and fast positioning of the target at the treatment time. In practice, the accuracy should be below 1 mm, and the computation time should be on the order of a few seconds. Unfortunately, it is difficult to meet both requirements simultaneously, because of a number of reasons. First, the two different image modalities (CT and x-ray) are characterized by different spatial resolution and image quality. X-ray image resolution and quality are generally superior to the resolution and quality of DRR images, which are only synthesized projection images. Second, DRR generation relies on a proper attenuation model. Because attenuation is proportional to mass intensity, the exact relationship between mass intensity and CT image intensity needs to be known for an accurate modeling. It is difficult to establish this relationship, however, so the linear attenuation model is often used. The skeletal structures in DRR images cannot be reconstructed very well when the linear model is used. Finally, x-ray images usually have a large image size (512×512). It is desirable to use full resolution images, for better registration accuracy. However, the full resolution of the x-ray images is rarely used, because of the extremely slow computation time that results from such use.

The methods used in the 2D/3D registration can be categorized into two types. The first type of methods is based on image features. The image features could be anatomical edges, for example, or segmented objects. The registration accuracy depends on the accuracy of edge detection or object segmentation. The main advantage of this type of method is the high computation speed. Because the full information content of the image is not used, however, accuracy is sacrificed. The second type of method is based on image intensity content. The original images are used for registration. Usually, a good accuracy can be achieved. Because a long time computation is required, however, image intensity based methods are not practical for radiosurgery, or for clinical practice in general.

U.S. Pat. No. 5,901,199 by Murphy et al. (the "Murphy patent") describes a high-speed inter-modality image registration via iterative feature matching. The Murphy patent is a feature-based method. Prior to treatment, extraction and segmentation of silhouettes of the patient's skull are performed in order to make a feature mask. A set of DRR images are generated from the 3D CT data and are then masked, in order to isolate key pixels that are associated with anatomical edge features. The masked image contains only 5%-10% of the total image pixels. During treatment, the acquired x-ray images are similarly masked. The registration is conducted on the masked DRRs and the masked X-ray images. The registration process is completed in a few seconds. However, the accuracy and stability of the estimates are not sufficient to meet the sub-mm precision that is required in radiosurgery applications.

For these reasons, there is a need for a method and system in image-guided radiosurgery for tracking the position of the treatment target, throughout the radiosurgical treatment procedure, with a computation time that is fast enough for purposes of radiosurgery, while at the same time maintaining sufficient accuracy and stability.

SUMMARY OF THE INVENTION

The present invention is directed to an accurate and rapid method and system for tracking target position for image guided radiosurgery. A hierarchical and iterative 2D/3D registration algorithm is used that allows for accurate and rapid correction of target position, and alignment of radiosurgical beams, throughout the treatment procedure.

A method in image guided radiosurgery is presented for aligning the position of a treatment target relative to a radiosurgical beam generator during treatment. The method includes generating a pre-treatment 3D scan of the target, which is treated as a rigid body with six degrees of freedom for describing its position. The 3D scan (for example a CT scan, an MRI scan, or a PET scan) shows the position of the target at treatment planning time. One or more 2D x-ray images of the target are generated at near real time. The x-ray images show the position of the target at a current time during treatment. Preferably, two orthogonal x-ray projections images are generated, using imaging beams having a known position, angle, and intensity. A set of 2D reconstructed images, preferably DRRs (digitally reconstructed radiographs), are generated offline, based on the 3D scan data and the known positions, angles, and intensities of the imaging beams.

The DRRs are registered with the x-ray images, using a hierarchical and iterative framework. The 3D rigid body transformation parameters, which represent the change in position of target between said 3D scan and the x-ray images, are generated. The registration is performed for each projection individually, and the results are subsequently combined. In-plane and out-of-plane transformation parameters are estimated using different search methods, including 3-D multi-level matching and 1-D searching, then iteratively refined until a desired accuracy is reached. The relative position of the radiosurgical beams and the target are continuously adjusted in near real time, throughout the treatment, in accordance with the 3D transformation parameters obtained via the 2D/3D registration process.

An image guided radiosurgical system is presented for radiosurgical treatment of a target, such as a human skull or other target region within a patient's anatomy. The system includes means for generating pre-treatment 3D scan data of the target, for example a CT scanner or an MRI system. A radiosurgical beam generator is provided for generating at least one radiosurgical beam for treating the target. Imaging means are provided for generating 2D x-ray images of the target in near real time. The imaging means include one or more (preferably two) imaging x-ray beam sources for generating at least one imaging beam having a known intensity, position and angle. The imaging beams are directed toward and through the target, and detected by corresponding image receivers (cameras) that detect the beams after the beams have traversed the target. The detection signals are processed by an image processor, which generates the x-ray images. Preferably, a pair of x-ray sources and a corresponding pair of x-ray cameras are provides, so that two orthogonal x-ray projection images are generated.

Means are provided for generating a set of 2D DRRs for each x-ray projection image. The DRRs are based on the 3D scan data, and generated using the known intensity, location, and angle of the imaging beams. Processing means are provided for registering the DRRs with the x-ray images. The processing means include a processor for computing a set of 3D transformation parameters that represent the change in position of the target between the 3D scan and the near real time x-ray images. The processor includes software for performing a 2D/3D registration algorithm that includes estimating in-plane and out-of-plane transformation parameters for each projection, using a number of search methods including 3D multi-level matching, 2D sub-pixel matching, and 1D searching, and using two different similarity methods (sum-of-square differences and pattern intensity) at different phases of the registration process. The radiosurgical system also including positioning means, responsive to a controller, for adjusting in near real time the relative position of the radiosurgical beams and the target, in accordance with the 3D transformation parameters obtained by the 2D/3D registration process.

DETAILED DESCRIPTION

The present invention features an accurate and rapid method and system for tracking the position of a treatment target in image-guided radiosurgery. The position of the target is tracked in six degrees of freedom. The present invention is useful for patient position correction and radiation beam alignment during radiosurgery/radiotherapy of a treatment target, for example a tumor within the brain or skull. The method and system of the present invention allows for a fully automatic tracking process, with no need for user interaction.

In overview, 2D reconstructed radiographs (typically, DRRs) are generated offline from a pre-treatment 3D scan. The 3D scan is typically a CT scan, however, any other 3D diagnostic scan (such as MRI or PET) may also be used. The DRRs are used as references for determining the position of the target. X-ray images are then acquired in near real time during treatment, in order to determine the change in target position. A hierarchical and iterative framework is used to register between the DRRs and X-ray images. The relative position of the radiosurgical beams and the target is continuously adjusted in near real time, in accordance with the results of the registration process, so that the radiosurgical beams remain properly focused onto the target throughout the treatment. By using different search methods for different transformation parameters, and by optimizing similarity measures for different phases of the registration procedure, an increased accuracy is achieved in the target tracking process, with a significantly reduced computing time.

In the present invention, the radiosurgery target is treated as a rigid body. As well known, a rigid body is defined as an object whose internal geometric relationships remain static or unchanged over time. Because there are no external forces imposed on a radiosurgical target during radiation treatment, it is reasonable to treat the target as a rigid body, and to use a 3D rigid transformation for the registration process. The 3D rigid transformation is described using six degrees of freedom: three translations along three mutually orthogonal axes in a 3D scan coordinate system (conventionally labeled as the x-, y-, and z-axes), and three rotations (roll, pitch, yaw) about these three axes. The six degrees of freedom are thus represented by six 3D transformation parameters: (x, y, z, r, p, w), where r represents the rotation about the x-axis, p represents the rotation about the y-axis, and w represents the rotation about the z-axis.

Figure 1:
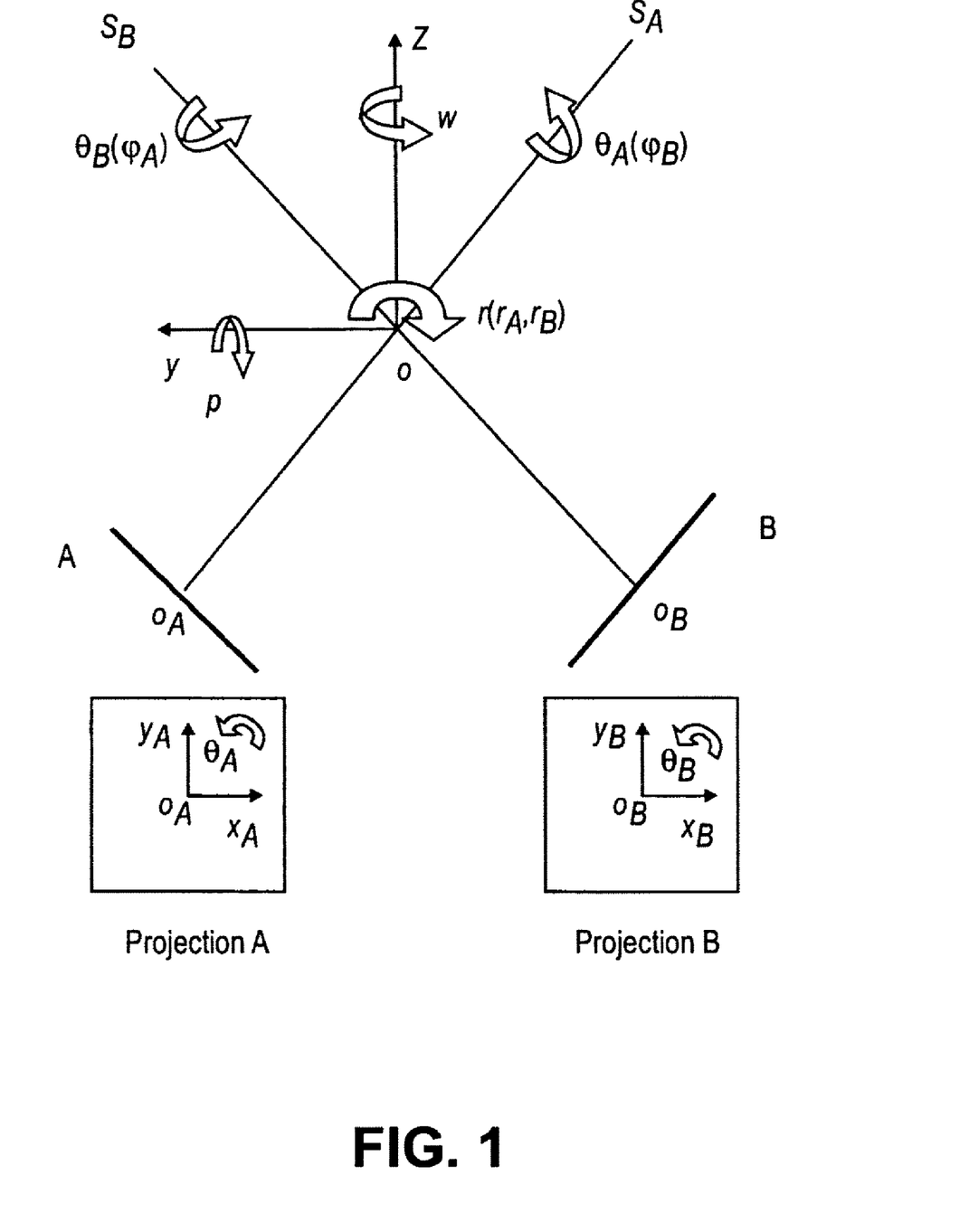
FIG. 1 illustrates the geometric relations between a 3D treatment target and two orthogonal x-ray projections, in an image-guided radiosurgery method and system in accordance with one embodiment of the present invention.

In the present invention, two orthogonal x-ray projections are used to solve for these six parameters. FIG. 1 illustrates the geometric relations between a three-dimensional treatment target, and two orthogonal 2D x-ray projections (labeled A and B in FIG. 1), in an image-guided radiosurgery method and system in accordance with the present invention. Cameras (or image receivers) A and B receive their x-ray projections from respective x-ray sources (not shown). In the 3D scan coordinate system, the x-axis is directed inward into the paper, and is not indicated in FIG. 1. As explained above, in the 3D coordinate system, the change in position of the target is represented by three translations and three rotations (x, y, z, r, p, w).

In FIG. 1, the orthogonal 2D projections A and B are viewed from the directions $o_A s_A$ and $o_B s_B$, respectively. For each of the projections A and B, FIG. 1 illustrates respective 2D planar coordinate systems that are fixed with respect to the image plane that characterizes each projection. The image planes A and B for the projections A and B are thus defined by mutually orthogonal axes within the respective coordinate systems. These axes are shown in FIG. 1 as $(x_A, y_A)$ for projection A, and $(x_B, y_B)$ for projection B. The direction of the axis $x_A$ in the 2D coordinate system for projection A, and the direction of the x-axis in the 3D scan coordinate system, are opposite with respect to each other. The direction of axis $x_B$ in the coordinate system for projection B, and the direction of the axis x in the 3D scan coordinate system, are the same.

As shown in FIG. 1, each projection is characterized by a respective set of transformation parameters, namely $(x_A, y_A, \theta_A, r_A, \phi_A)$ for projection A, and $(x_B, y_B, \theta_B, r_B, \phi_B)$ for projection B. The two out-of-plane rotations (with respect to the image plane) in projections A and B are denoted by $(r_A, \phi_A)$ and $(r_B, \phi_B)$ respectively, where r denotes the amount of rotation about the x-axis (in the 3D scan coordinate system), and $\phi$ denotes the amount of rotation about the $o_A s_A$ axis (for projection B) or the $o_B s_B$ axis (for projection A). The in-plane translations and rotation in projections A and B are denoted $(x_A y_A \theta A)$ and $(x_B y_B \theta_B)$, respectively. As easily seen, $(x_A y_A)$ and $(x_B y_B)$ denote the amount of translations within the image planes for each projection (A and B) in the directions of the x- and y-axes that define each image plane ($x_A$- and $y_A$- for projection A, and $x_B$- and $y_B$ for projection B), while $\theta_A$ and $\theta_B$ denote the amount of rotation within each image plane about an axis (not shown) that is perpendicular to both the $x_A$- (or $x_B$-) and $y_A$- (or $y_B$-) axes.

As can be seen from FIG. 1, the out-of-plane rotation $\phi_A$ in projection A is the same as the in-plane rotation $\theta_B$ in projection B, and the out-of-plane rotation $\phi_B$ in projection B is the same as the in-plane rotation $\theta_A$ in projection A. The use of the two projections A and B thus over-constrains the problem of solving for the six degrees of freedom. As seen from FIG. 1, $x_A = x_B$, $r_A = r_B$, $\theta_A = \phi_B$ and $\theta_B = \phi_A$.

Figure 2:
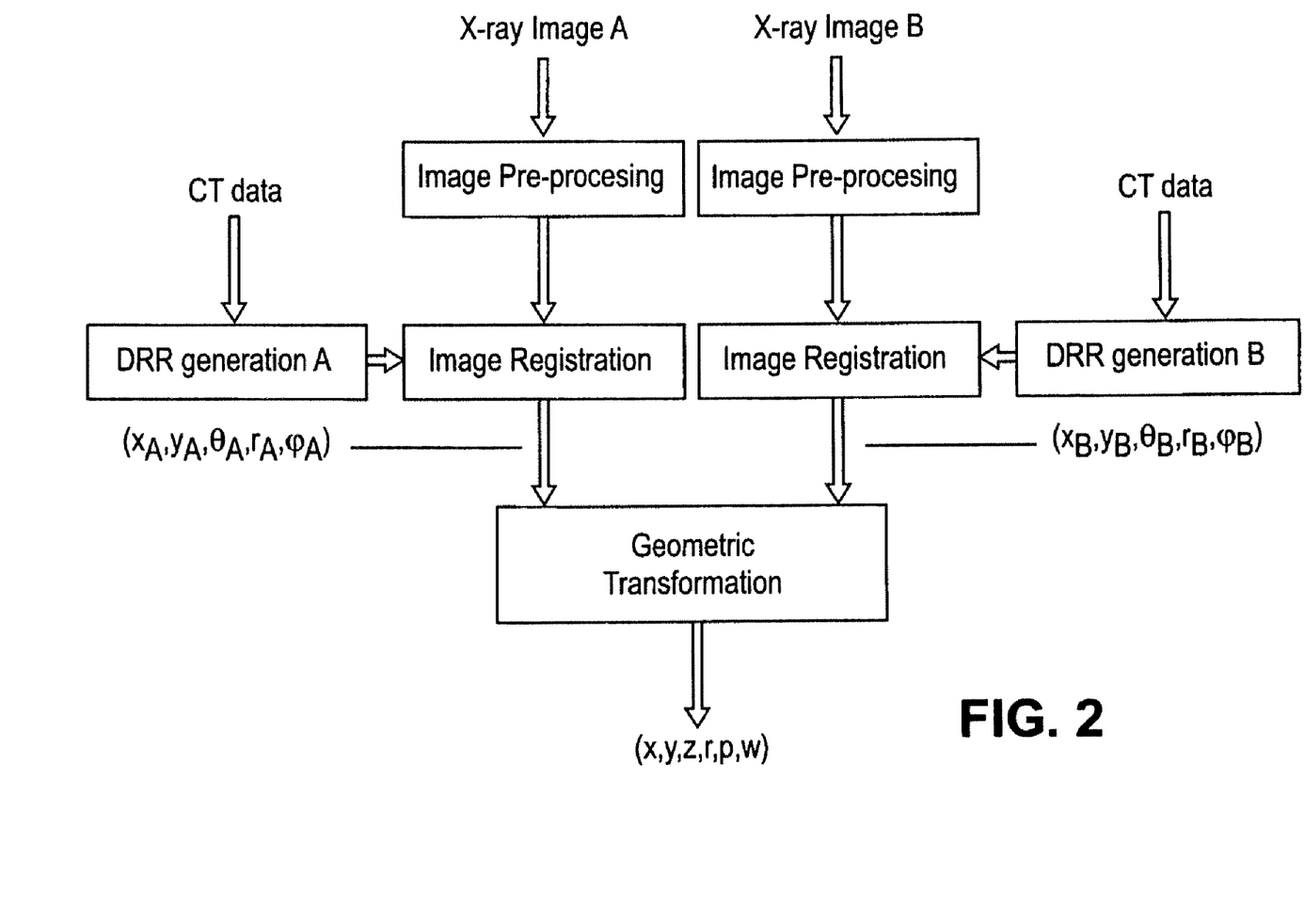
FIG. 2 is a schematic diagram of a methodology for tracking a treatment target during image-guided radiosurgery, in accordance with one embodiment of the present invention.

FIG. 2 is a schematic diagram of a methodology for tracking a treatment target during image-guided radiosurgery, in accordance with one embodiment of the present invention. In overview, two sets of DRRs (or other 2D reconstructed images, for example) are generated in the present invention, one set for each of the projections A and B. The process of generating DRRs is carried out after the radiation treatment planning is completed, but before treatment delivery. Before patient treatment, DRR initialization is performed on the initial DRRs, to create a set of in-plane rotated reference DRR images. In the course of radiosurgical treatment, the real time x-ray projection images are acquired and pre-processed. The processed x-ray images for each projection are registered with the corresponding set of reference DRR images. The results of the registration, $(x_A, y_A, \theta_A, r_A, \phi_A)$ and $(x_B, y_B, \theta_m, r_B, \phi_B)$ for projections A and B, are combined to produce the final six rigid transformation parameters (x, y, z, r, p, w).

The step of generating DRRs is performed offline, and involves specifying a set of rotation angles for each of the out-of-plane rotations r and $\phi$, for each projection A and B. Each set of DRRs for each projection includes DRRs that correspond to different combinations of these out-of-plane rotation angles. Therefore, the total number of DRR images is therefore $N_r * N_\phi$, where $N_r$ and $N_\phi$ respectively denote the number of rotation angles for the two out-of-plane rotations r and $\phi$. Because the out-of-plane rotations are expected to approach zero after patient alignment, the angles are more densely sampled in the range close to zero, and more sparsely sampled in the range of larger rotation angles.

Once the DRRs for out-of-plane rotations are generated, DRR initialization is performed, by computing a set of in-plane rotated reference DRRs images (in 0 degree). The most intensive part of computation in registration is the in-plane rotation computation. To achieve a fast computation, therefore, it is desirable to compute as many as possible in-plane rotations for the reference DRRs, before the registration process. All the reference DRR images are stored in a memory unit in the radiosurgical system, and are used for registration in each x-ray image acquisition, during target alignment and treatment.

The 2D x-ray images of the target that represent the two orthogonal projections A and B onto the respective image planes (shown in FIG. 1) are acquired in near real time, by transmitting respective imaging beams through the target and onto the cameras A and B. The imaging beams for each projection (attenuated by virtue of having passed through the target) are detected by the respective cameras, after passing through the target. The detection signals are sent to an image sensor, so that the 2D x-ray projection images are generated. The raw 2D x-ray images are pre-processed, before beginning the 2D/3D registration process. Pre-processing the raw x-ray images is necessary, in order to make the x-ray and DRR images have the same orientation, same image size, and same bit depth.

For projection A, given a set of reference DRR images which correspond to different combinations of the two out-of-plane rotations $(r_A, \phi_A)$, the 2D in-plane transformation $(x_A, y_A, \phi_A)$ can be estimated by the 2D image comparison. Determining the two out-of-plane rotations $(r, \theta_B)$ relies on which reference DRR is used for an optimal similarity match. Similarly, the 2D in-plane transformation $(x_B, y_B, \theta_B)$ and the out-of-plane rotations $(r_B, \phi_B)$ can be estimated for projection B. Given the results $(x_A, y_A, \theta_A, r_A, \phi_A)$ for projection A and $(x_B, y_B, \theta_B, r_B, \phi_B)$ projection B, the 3-D transformation can be obtained by the following expressions $$x=(x_A+x_B)/2, y=(y_A-y_B)/\sqrt{2}, z=(y_A+y_B)/\sqrt{2},$$

$$r=(r_A+r_B)/2, p=(\theta_B-\theta_A)/\sqrt{2}, w=(\theta_B+\theta_A)/\sqrt{2},$$

In the present invention, the 2D/3D registration process uses a registration algorithm that is designed in a unique hierarchical and iterative framework.

The 2D/3D registration process is described in detail in co-pending patent application (submitted on the same day as the current application, and identified by attorney docket number ACCL-125), which is owned by the assignee of the present application and hereby incorporated by reference in its entirety. The similarity measures used in this 2D/3D registration process is described in detail in co-pending patent application (submitted on the same day as the current application, and identified by attorney docket number ACCL-127), which is owned by the assignee of the present application and hereby incorporated by reference in its entirety.

It has been observed that the out-of-plane rotations can be detected with a good accuracy only after the in-plane parameters have already been well estimated. It has also been found that the out-of-plane rotations are able to safely converge to the correct values when starting from the nominal position of the DRRs. Accordingly, a separate computation is carried out for the out-of-plane versus in-plane transformation parameters, during the registration process: the two out-of-plane rotations $(r, \phi)$ are estimated from the exact reference DRR images, while the in-plane transformation parameters $(x, y, \theta)$ are computed directly from the 2D images. The in-plane parameters $(x, y, \theta)$ are first computed using the nominal reference DRRs. An initial estimate for the out-of-plane rotations $(r, \phi)$ is then carried out, based on the previously obtained values of the in-plane transformation parameters $(x, y, \theta)$. In order to maximize efficiency and accuracy, different search strategies are used for estimating the out-of-plane transformations and the in-plane transformations, respectively. Also, multiple similarity measure criteria are used that have been optimized at the different phases during the registration.

In an exemplary embodiment of the present invention, the registration process is described in terms of six distinct phases. In phase 1, the in-plane transformation parameters $(x, y, \theta)$ are initially estimated using the in-plane rotated DRR images, which are generated offline from the nominal reference DRR. Using a sum of absolute differences method (SAD; described in the co-pending ACCL-127 application) as the similarity measure, the three parameters are rapidly searched by a 3-D multi-level matching method. In this phase, there is no floating computation. The pixel accuracy for translations and half-degree accuracy for in-plane rotation are achieved.

In phase 2, based on the values of $(x, y, \theta)$ determined in the first phase described above, the two out-of-plane rotations $(r, \phi)$ are separately searched in one dimension. A more complicated similarity measure, based on pattern intensity, is used to detect the reference DRR image that corresponds to a combination of the two out-of-plane rotations $(r, \phi)$. The search space for the possible rotation angles is the full search range of out-of-plane rotation angles. As the initial estimation, the full search range is sampled at every one-degree interval.

In phase 3, the in-plane translation parameters $(x, y)$ are refined using 2-D sub-pixel matching. In phase 4, the in-plane rotation parameter $\theta$ is refined using 1-D interpolation, based the updated values for the in-plane translation parameters $(x, y)$ and the out-of-plane rotation parameters $(r, \phi)$. In phase 5, the out-of-plane rotations are separately refined to a better accuracy using a 1D search, based the updated in-plane transformation $(x, y, \theta)$. In phases 3, 4, and 5, similarity measure method based on pattern intensity is used, to ensure a higher accuracy.

Phases 3, 4 and 5 are iteratively repeated until a sufficient accuracy is obtained. Once the desired accuracy is reached, the final out-of-plane rotations are 1-D interpolated, in the final phase 6 of the registration process. In practice, a high accuracy is obtained for both translations and rotations, using the method and system of the present invention. For translations, an accuracy of 0.5 mm or better is reached, and for rotations an accuracy of 0.5 degrees or better is reached. The total computing time is a few seconds, which is an order of magnitude faster than other methods in the prior art.

Figure 3:
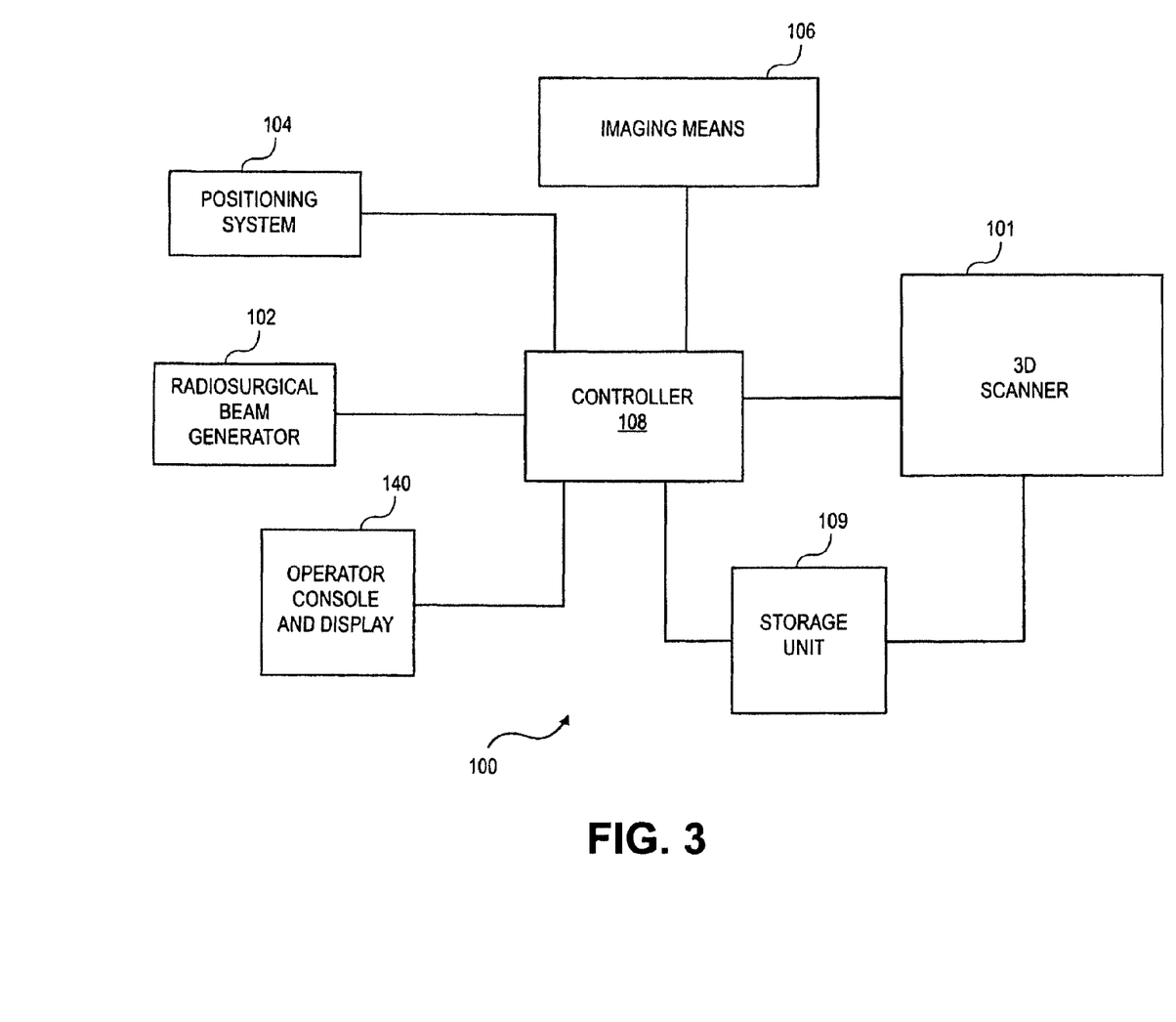
FIG. 3 schematically illustrates an image-guided radiosurgery system, constructed in accordance with one embodiment of the present invention.

FIG. 3 schematically illustrates an image-guided radiosurgery system, constructed in accordance with one embodiment of the present invention. In overview, the image guided radiosurgery system 100 includes a means 101 for generating pre-treatment 3D scan data of the target; radiosurgical beam generator 102; a positioning system 104; imaging means 106; and a controller 108. The system 100 may also include an operator control console and display 140. The means 101 may be a CT scanner, for example, or an MRI system or a PET system.

The radiosurgical beam generator 102 generates, when activated, a plurality of collimated radiosurgical beam (e.g. x-ray beam). The cumulative effect of the radiosurgical beams, when properly directed to and focused onto the target, is to necrotize or perform other treatments in a target within the patient's anatomy. The positioning system 104 may be an industrial robot, by way of example, and the beam generator 102 may be a small x-ray linac mounted to an arm of the industrial robot 104.

The imaging means 106 is preferably an x-ray imaging system for generating a pair of orthogonal x-ray projection images of the target. The imaging means 106 preferably has a pair of x-ray sources for generating diagnostic imaging beams (having known positions, angles, and intensities), and a corresponding pair of x-ray image detectors which detect the beams after the beams have passed through the target.

The controller 108 includes software for generating a set of reconstructed 2D images (preferably DRRs) of the target, based on the 3D scan data from the 3D scanner 101, and the known intensity, location, and angle of the imaging beams. The controller 108 includes software for registering the DRRs with the real time x-ray images. The registration software is able to compute a set of 3D transformation parameters that represent the change in position of the target between the 3D scan and the near real-time x-ray images.

The positioning system 104 is responsive to commands from the controller 108, to continuously adjust, in near real time, the relative position of the radiosurgical beam generator and the target by the amount prescribed by the 3D transformation parameters obtained through the registration process.

The method and system of the present invention provide numerous advantages over the prior art. In the present invention, for example, a fully automatic tracking process is achieved, and no user intervention is necessary. Also, the registration process is optimized to allow the use of images having a full resolution. In this way, the full informational content of each image can be utilized, without having to leave out any image features. These results are achieved while reducing the total computation time for the tracking process to a few seconds, which is an order of magnitude faster than the existing prior art methods. At the same time, a high accuracy is achieved for both the translation parameters (below about 0.5 mm) and the rotation parameters (below about 0.5 degrees).

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method comprising:
   generating a set of 2D reconstructed images from a pre-treatment 3D scan showing an initial position of a target, wherein the set of 2D reconstructed images corresponds to perturbations from said initial position along fewer than six degrees of freedom;
   registering said set of 2D reconstructed images with one or more 2D x-ray images of said target showing a current position of the target, wherein the registering includes computing a set of 3D transformation parameters that represent a change in position of said target between said initial position of said pretreatment 3D scan and said current position of said 2D x-ray images along six degrees of freedom; and instructing a positioning system to adjust a relative position of a radiosurgical beam generator to said target by an amount prescribed by said 3D transformation parameters, wherein said target is allowed six degrees of freedom of position.

2. The method of claim 1, wherein said set of 2D reconstructed images include a first subset of 2D reconstructed images associated with a first image plane of a first 2D x-ray image and a second subset of 2D reconstructed images associated with a second image plane of a second 2D x-ray image.

3. The method of claim 2, wherein registering said set of 2D reconstructed images with said 2D x-ray images comprises:

registering the first 2D x-ray image with the first subset of 2D reconstructed images by determining a first set of transformation parameters that represent a change in position of said target between said initial position of said pretreatment 3D scan and said current position of said first 2D x-ray image along fewer than six degrees of freedom;

registering the second 2D x-ray image with the second subset of 2D reconstructed images by determining a second set of transformation parameters that represent a change in position of said target between said initial position of said pretreatment 3D scan and said current position of said second 2D x-ray image along fewer than six degrees of freedom; and combining the first set of transformation parameters with the second set of transformation parameters to obtain said 3D transformation parameters along six degrees of freedom.

4. The method of claim 3, wherein said first set of transformation parameters and said second set of transformation parameters each include two out-of-plane rotational parameters and three in-plane transformation parameters.

5. The method of claim 3, wherein the first set of transformation parameters represents a first five degrees of freedom, and the second set of transformation parameters represents a second five degrees of freedom, at least one of the first five degrees of freedom overlapping one of the second five degrees of freedom.

6. The method of claim 1, wherein the first set of 2D reconstructed images correspond to perturbations from said initial position along up to two degrees of freedom and the second set of 2D reconstructed images correspond to perturbations from said initial position along up to two degrees of freedom.

7. The method of claim 1, wherein the registering is performed in a plurality of search phases using combinations of search techniques and similarity measures in each search phase.

8. The method of claim 1, wherein the registering comprises:

estimating in-plane transformation parameters between the 2D x-ray images of the target and the set of 2D reconstructed images of the target in a first search phase; and estimating out-of-plane rotation parameters between the 2D x-ray images of the target and the set of 2D reconstructed images of the target in a second search phase.

9. The method of claim 8, wherein the in-plane transformation parameters are estimated using a first similarity measure and a first search method and wherein the out-of-plane rotation parameters are estimated using a second similarity measure and a second search method.

10. The method of claim 9, further comprising:

using at least one of a third similarity measure or a third search method to iteratively refine a registration accuracy between the 2D x-ray images of the target and the set of 2D reconstructed images of the target.

11. A system comprising:

a controller having a processing device, the processing device to execute instructions for performing image registration, wherein the instructions cause the processing device to:

generate a set of 2D reconstructed images from a pretreatment 3D scan showing an initial position of a target, wherein the set of 2D reconstructed images corresponds to perturbations from said initial position along fewer than six degrees of freedom;

register said set of 2D reconstructed images with one or more 2D x-ray images of said target showing a current position of the target, wherein the registering includes computing a set of 3D transformation parameters that represent a change in position of said target between said initial position of said pretreatment 3D scan and said current position of said 2D x-ray images along six degrees of freedom; and determine an adjustment to make to a relative position of a radiosurgical beam generator to said target based on said 3D transformation parameters, wherein said target is allowed six degrees of freedom of position.

12. The system of claim 11, wherein said set of 2D reconstructed images include a first subset of 2D reconstructed images associated with a first image plane of a first 2D x-ray image and a second subset of 2D reconstructed images associated with a second image plane of a second 2D x-ray image.

13. The system of claim 12, wherein registering said set of 2D reconstructed images with said 2D x-ray images comprises:

registering the first 2D x-ray image with the first subset of 2D reconstructed images by determining a first set of transformation parameters that represent a change in position of said target between said initial position of said pretreatment 3D scan and said current position of said first 2D x-ray image along fewer than six degrees of freedom;

registering the second 2D x-ray image with the second subset of 2D reconstructed images by determining a second set of transformation parameters that represent a change in position of said target between said initial position of said pretreatment 3D scan and said current position of said second 2D x-ray image along fewer than six degrees of freedom; and combining the first set of transformation parameters with the second set of transformation parameters to obtain said 3D transformation parameters along six degrees of freedom.

14. The system of claim 13, wherein said first set of transformation parameters and said second set of transformation parameters each include two out-of-plane rotational parameters and three in-plane transformation parameters.

15. The system of claim 13, wherein the first set of transformation parameters represents a first five degrees of freedom, and the second set of transformation parameters represents a second five degrees of freedom, at least one of the first five degrees of freedom overlapping one of the second five degrees of freedom.

16. The system of claim 11, wherein the instructions cause the processing device to perform the registering in a plurality of search phases using combinations of search techniques and similarity measures in each search phase.

17. The system of claim 11, wherein the registering comprises:
  estimating in-plane transformation parameters between the 2D x-ray images of the target and the set of 2D reconstructed images of the target in a first search phase using a first similarity measure; and
  estimating out-of-plane rotation parameters between the 2D x-ray images of the target and the set of 2D reconstructed images of the target in a second search phase using a second similarity measure.

18. The system of claim 11, further comprising:
  the radiosurgical beam generator, to generate a collimated radiosurgical beam; and
  a positioning system, to receive commands from the controller to adjust the relative position of the radiosurgical beam generator to said target, and to adjust the relative position of the radiosurgical beam generator to said target based on the received commands.

19. The system of claim 11, further comprising: means for generating the pretreatment 3D scan.

20. The system of claim 11, further comprising:
  an imaging system, including one or more x-ray sources, to generate the one or more 2D x-ray images.

* * * * *